United States Patent [19]

White

[11] Patent Number: 4,730,066

[45] Date of Patent: Mar. 8, 1988

[54] COMPLEX FOR ENHANCING MAGNETIC RESONANCE IMAGING

[75] Inventor: David H. White, St. Louis, Mo.

[73] Assignee: Mallinckrodt, Inc., St. Louis, Mo.

[21] Appl. No.: 860,064

[22] Filed: May 6, 1986

[51] Int. Cl.$^4$ ............................................. C07F 11/00
[52] U.S. Cl. ........................................ 556/50; 556/63;
534/16; 436/173
[58] Field of Search ....................... 556/50, 63; 534/16

[56] References Cited

U.S. PATENT DOCUMENTS 4,472,509  9/1984  Gansow et al. ..................... 436/548

OTHER PUBLICATIONS

Brasch et al, AJR 142, 625–630 (1984).

Primary Examiner—Helen M. S. Sneed
Attorney, Agent, or Firm—Senniger, Powers, Leavitt and Roedel

[57] ABSTRACT

Complexes of iron(II), iron(III), manganese(II), manganese(III), gadolinium(III) or chromium(III) and a compound of the formula:

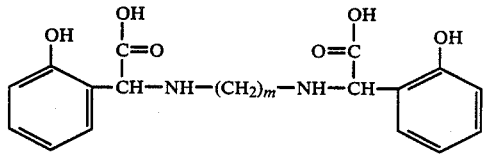

wherein m=2, 3, 4, or 5, are useful for enhancing magnetic resonance images of body organs and tissues, such as magnetic resonance images of the hepatobiliary system. An illustrative complex of this type is monosodium [ethylenediamine-di(o-hydroxyphenylaceto)]iron(III) hydrate.

1 Claim, No Drawings

COMPLEX FOR ENHANCING MAGNETIC RESONANCE IMAGING

BACKGROUND OF THE INVENTION

This invention relates to magnetic resonance imaging (MRI), also referred to as nuclear magnetic resonance (NMR) imaging, and more particularly, to methods and composition for enhancing magnetic resonance images of body organs and tissues.

The recently developed techniques of MRI or NMR imaging encompass the detection of certain atomic nuclei utilizing magnetic fields and radio-frequency radiation. It is similar in some respects to x-ray computed tomography (CT) in providing a cross-sectional display of the body organ anatomy with excellent resolution of soft tissue detail. In current use, the images produced constitute a map of the distribution density of protons and/or their relaxation times in organs and tissues. The MRI technique is advantageously non-invasive as it avoids the use of ionizing radiation.

While the phenomenon of NMR was discovered in 1945, it is only relative recently that it has found application as a means of mapping the internal structure of the body as a result of the original suggestion of Lauterbur (Nature, 242, 190–191, 1973). The lack of any known hazard associated with the level of the magnetic and radio-frequency fields that are employed renders it possible to make repeated scans on vulnerable individuals. Additionally, any scan plane can readily be selected including transverse, coronal, and sagittal sections.

In an NMR experiment, the nuclei under study in a sample (e.g. protons) are irradiated with the appropriate radio-frequency (RF) energy in a highly uniform magnetic field. These nuclei as they relax subsequently emit RF radiation at a sharp resonant frquency. The emitted frequency (RF) of the nuclei depends on the applied magnetic field.

According to known principles, nuclei with appropriate spin when placed in an applied magnetic field [B, expressed generally in units of gauss or tesla ($10^4$ gauss)] align in the direction of the field. In the case of protons, these nuclei precess at a fequency f=42.6 MHz at a field strength of 1 Telsa. At this frequency, an RF pulse of radiation will excite the nuclei and can be considered to tip the nuclei out of the field direction, the extent of this rotation being determined by the pulse duration and energy. After the RF pulse, the nuclei "relax" or return to equilibrium with the magnetic field,. emitting radiation at the resonant frequency. The decay of the signal is characterized by two relaxation times, i.e., $T_1$, the spin-lattice relaxation time or longitudinal relaxation time, that is, time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thickness can be selected without loss of resolution. This permits high quality transverse, coronal and sagittal images to be obtained directly. The absence of any moving parts in MRI equipment promotes a high reliability. It is believed that MRI or NMR imaging has a greater potential than CT for the selective examination of tissue characteristics in view of the fact that in CT, x-ray attenuation coefficients alone determine image contrast whereas at least four separate variables ($T_1$, $T_2$, nuclear spin density and flow) may contribute to the NMR signal. For example, it has been shown (Damadian, Science, 171, 1151, 1971) that the values of the $T_1$ and $T_2$ relaxation in tissues are generally longer by about a factor of 2 in excised specimens of neoplastic tissue compared with the host tissue.

By reason of its sensitivity to subtle physio-chemical differences between organs and/or tissues, it is believed that MRI may be capable of differentiating tissue types and in detecting diseases which induce physio-chemical changes that may not be detected by x-ray or CT which are only sensitive to differences in the electron density of tissue. The images obtainable by MRI techniques also enable the physician to detect structures smaller than those detectable by CT and thereby provide comparable or better spatial resolution.

Continuing efforts are being made to develop imaging agents for enhancing the images obtained through the use of MRI techniques.

SUMMARY OF THE INVENTION

Among the several objects of the invention may be noted the provision of novel complexes of certain ligands with one or more central metal ions for use in enhancing magnetic resonance images of body organs and tissues; the provision of such metal complexes which exhibit favorable toxicity profiles; and the provision of methods for enhancing magnetic resonance images of body organs and tissues through the administration of such complexes. Other objects and features will be in part apparent and in part pointed out hereinafter.

Briefly, the invention is directed to complexes comprised of one or more central metal ions of the group consisting of iron(II), iron(III), manganese(II), manganese(III), gadolinium(III) and chromium(III) and a compound of the formula:

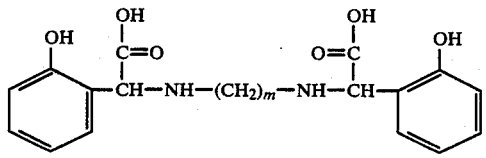

wherein m=2, 3, 4 or 5. The invention is also directed to methods for enhancing magnetic resonance images of body organs and tissues by administering such complexes to a mammal in sufficient amounts to provide enhancement of magnetic resonance images of the body organs and tissues.

DESCRIPTION OF THE PREFERRED EMBODIMENTS

In accordance with the present invention, it has now been found that magnetic resonance images of body organs and tissues may be usefully enhanced through the administration to a mammal of substantially nontoxic metal complexes of a compound of the formula:

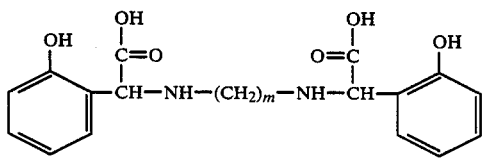

wherein m=2, 3, 4 or 5.

Complexes of the ligands or compounds of the above class with one or more central metal ions such as iron(II), iron(II), manganese(II), manganese(III), gadolinium(III) and chromium(III) are useful for enhancing magnetic resonance images. While such metal ions are themselves paramagnetic in nature and capable of altering the magnetic resonance signal characteristics of body tissues, organs or fluids, they may undesirably exhibit significant toxicity when administered in the form of ionic salts. However, it has been found that the novel complexes of the present invention are relatively or substantially nontoxic and are therefore useful for enhancing magnetic resonance images by favorably altering relaxation times $T_1$ and $T_2$ and thereby affording improved contrast between normal and diseased tissues or organs.

The preferred complexes of the invention are those formed from the above ligands or compounds and iron(II), iron(III), manganese(II), manganese(III) and gadolininium(III) as the central metal ion or ions. The negatively charged complexes formed by the ligands and central metal ions enumerated above may be further complexed with one or more cations of an inorganic or organic base which are physiologically tolerated such as sodium, potassium, calcium, N-methylglucamine or diethanolamine.

The preferred ligand is one in which m=2, i.e. ethylenediamine-di(o-hydroxyphenylacetic acid), although other ligands of the above formula may also be employed. Illustrative complexes of such ligand and one or more central metal ions from the group consisting of iron(II), iron(III), manganese(II), manganese(III), gadolinium(III) and chromium(III) include monosodium [ethylenediamine-di-(o-hydroxyphenylaceto)]iron(III) hydrate, monosodium [ethylenediamine-di(o-hydroxyphenylaceto)]manganese(III), and monosodium[ethylenediamine-di(o-hydroxyphenylaceto)]gadolinium(III). The complexes are formed by reacting the ligand with a metal salt or oxide, the metal being complexed as central metal ions with the carboxylic acid groups of the ligand.

As shown by the toxicity studies set forth hereinafter, a representative metal complex of the invention, namely, monosodium [ethylenediamine-di(o-hydroxyphenylaceto)]iron(III) hydrate, possesses a favorable intravenous toxicity profile and has an $LD_{50}$ value of greater than 5.18 mmol/kg. as compared with an $LD_{50}$ of approximately 7.2 mmol/kg. for the paramagnetic chelate disodium (diethylenetriaminepentaaceto)-gadolinium(III), ($GdNa_2DTPTA$), a relatively safe agent for use in magnetic resonance imaging. This metal complex of the invention also favorably influences relaxation times.

The substantially nontoxic metal complexes of the present invention are administered to a mammal in a sufficient amount to provide enhancement of magnetic resonance images of body organs and tissues prior to obtaining a magnetic resonance scan and scans of such organs and tissues with "slices" being taken at the level of the desired organ at various time periods post-administration. The complexes of the invention may be used, for example, for enhancing magnetic resonance images of the hepatobiliary system.

The following examples illustrate the practice of the invention.

EXAMPLE 1

Preparation of Monosodium [ethylenediamine-di(o-hydroxyphenylaceto)]iron(III) Hydrate Methanol (36 ml) and ethylenediamine-di(o-hydroxyphenylacetic acid) (3.6 g) were added into a flask under a nitrogen blanket. The solution was stirred and aqueous $FeCl_3.6H_2O$ (2.7 g) solution ($H_2O$, 36 ml) was added dropwise over a period of 30 minutes. The solution was then refluxed for 30 minutes and filtered when hot to remove unreacted ligand. The filtrate was cooled to 25° C. and NaOH solid (1.6 g) was added. The mixture was stirred until all NaOH dissolved. The solution was cooled to 0° C. and added dropwise into acetone (750 ml) with vigorous stirring to precipitate the product. After stirring for 1 hr, the product monosodium [ethylenediamine-di(o-hydroxyphenylaceto)]iron(III) hydrate was collected and dried at 70° L C. Yield 2.4 g (47%). The product was a reddish brown crystal. Tlc analysis: two spots using the upper layer of nBuOH-$H_2O$-AcOH(4/1/5) system on a silica gel plate. Rf: 0.38 and 0.47.

Elemental analysis: Calculated for $C_{18}H_{16}N_2O_6$·$NaFe.4H_2O$: C, 42.62; H, 4.77; N, 5.52; Na, 4.53; Fe, 11.01. Found: C, 42.16; H, 4.83; N, 5.38; Na, 4.38; Fe, 11.74.

The relaxation times from a $9.99 \times 10^{-4}M$ solution in 25% $D_2O/H_2O$ in a 90 MHz NMR experiment were determined to be: $T_1=741$ msec; $1/T_{11}=0.00135$ msec$^{-1}$; $T_2=85$ msec; $1/T_2=0.0118$ msec$^{-1}$.

EXAMPLE 2

Acute Intravenous Toxicity Determination

An acute intravenous toxicity study was carried out with the complex of Example 1.

Dilutions of the complex were prepared as necessary using Sterile Water for Injection, U.S.P. (Abbott Laboratories, North Chicago, Ill.).

Male and female CF1, SQC strain, albino mice (males 16.6–24.9 g in weight; females 18.1–22.8 g in weight) were used. The mice were housed according to standard operating procedures and individually marked with picric acid for identification.

The mice (1 to 6 per dose level) with sexes equally represented received single intravenous injections of the complex of Example 1 via a lateral tail vein at 1.0 ml/min and were observed immediately after dosing and during the 7-day observation period for pharmatoxic reactions.

An estimated $LD_{50}$ value was calculated with an IBM XT computer using a modified Behrens-Reed-Muench Method (Drug Chem. Toxicol. 4:297–305, 1981).

The complex of Example 1, injected as a 5% w/v solution, was found to have an estimated (calculated) $LD_{50}$ value of greater than 5.18 mmol/kg. No immediate (0.1–1.0 hr) toxic reactions were noted following injections of the complex of Example 1. However, mild hypoactivity was observed by 4 hours post-administration. All animals appeared normal by the following day and throughout the 7-day observation period. The complex caused a magenta discoloration of the tail, feet, eyes, nose and internal pinna of the ear almost immediately following injection. The intensity of the color appeared to be dose-related. Within 5 minutes post-injection, magenta-colored urine spots appeared on the floor shavings of the holding containers; again color intensity appeared dose-related. Transient discoloration of highly vascularized external appendages and mild hypoactivity were observed during the first 24 hours post-injection. The discoloration was transient with no apparent signs by 24 hours post-injection. All animals exhibited weight gains during the observation period. Gross examination of internal organs at necropsy was unremarkable. At the maximum dose injected, the complex of Example 1 appears relatively safe.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A complex for use in enhancing magnetic resonance images of body organs and tissues, said complex comprising a central metal ion selected from the group consisting of manganese(II), manganese(III), gadolinium(III) and chromium(III) and a compound of the formula:

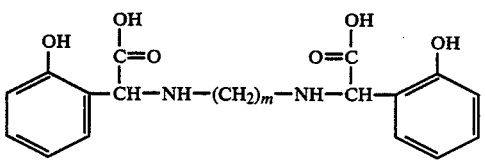

wherein $m = 2, 3, 4$ or $5$.